United States Patent [19]

Yelland

[11] 4,257,977

[45] Mar. 24, 1981

[54] 2-NITRO-4'-AMINODIPHENYLAMINE-2',4-DISULFONIC ACID AND PROCESS FOR ITS PREPARATION

[75] Inventor: Michael Yelland, Manchester, England

[73] Assignee: Imperial Chemical Industries Limited, London, England

[21] Appl. No.: 768,623

[22] Filed: Feb. 14, 1977

[30] Foreign Application Priority Data

Mar. 10, 1976 [GB] United Kingdom ................. 9515/76

[51] Int. Cl.³ .......................................... C07C 143/58
[52] U.S. Cl. ..................................... 260/510; 260/144
[58] Field of Search ........................................ 260/510

[56] References Cited

U.S. PATENT DOCUMENTS

| 869,073 | 10/1907 | Erdmann et al. | 260/510 |
| 3,248,379 | 4/1966 | Stanley | 260/199 |

OTHER PUBLICATIONS

Ridyard, Chem. Abstract, 82, 141,598f, (1975), (Ger. Offen. 2,421,579–11/21/74).
Howard et al., Chem. Abstract, 55, 3078e, (1961), (Brit. 838,338–6/22/60).
Imperial, Chem. Abstract, 58, 4671f, (1963), (Belg. 610,754–5/24/62).
Froehlich, Chem. Abstract, 76, 87187g, (1972), (Ger. Offen. 2,121,176–11/18/71).

Primary Examiner—Nicky Chan
Attorney, Agent, or Firm—Cushman, Darby & Cushman

[57] ABSTRACT

2-Nitro-4'-aminodiphenylamine,2',4-disulphonic acid, a new intermediate for azo dyes, is prepared by the monosulphonation of 2-nitro-4'-aminodiphenylamine-4-sulphonic acid or 2-nitro-4'-acetylaminodiphenylamine-4-sulphonic acid.

3 Claims, No Drawings

2-NITRO-4'-AMINODIPHENYLAMINE-2',4-DISULFONIC ACID AND PROCESS FOR ITS PREPARATION

This invention relates to a new chemical compound.

According to the invention there is provided, as a new chemical compound, 2-nitro-4'-aminodiphenylamine-2',4-disulphonic acid.

The new compound may be prepared by the monosulphonation of 2-nitro-4'-aminodiphenylamine-4-sulphonic acid or 2-nitro-4'-acetylaminodiphenylamine-4-sulphonic acid. Standard sulphonation conditions may be used, preferably using sulphuric acid having a strength of at least 95%, and including oleum of up to 20% strength, and temperatures in the range of $-10°$ to 80° C. It will be appreciated by those skilled in the art that the lower strengths of acid will most suitably be used at the higher temperatures and the higher strengths at the lower temperatures. It is preferred to use sulphuric acid of 100% strength or oleum of up to 10% strength at a temperature in the range 0° to 25° C. If desired, the 2-nitro-4'-aminodiphenylamine-2'-4-disulphonic acid may be isolated in the form of one of its salts, for example an alkali metal or ammonium salt.

The new acid and its salts may be used as a diazo component in the manufacture of azo dyes.

The invention is illustrated but not limited by the following Examples in which all parts and percentages are by weight.

EXAMPLE 1

154.5 Parts of 2-nitro-4'-aminodiphenylamine-4-sulphonic acid are added slowly to 650 parts of 100% sulphuric acid keeping the reaction temperature below 10° C. by external cooling. The mixture is stirred at 5°–10° C. for 2 hours and 284 parts of 20% oleum are added dropwise at 5°–10° C. The mixture is stirred for a further 1 hour at 5°–10° C. and for 1½ hours at 20°–25° C. The mixture is poured onto the minimum amount of ice required so that the final temperature of the resulting suspension is less than 40° C. Ammonia gas is passed into the mixture until the pH of the mixture is 8 and the precipitated product is filtered off. The filter cake is dissolved in 1 liter of water at 30° C. and the solution is acidified by the addition of 60 parts of 35.3% hydrochloric acid. The solution is screened and the filtrate is salted to a concentration of 10% by the addition of potassium chloride. The pH of the suspension is raised to 8 by the addition of potassium hydroxide solution and the product is filtered off and dried. Analysis Result: Found C, 28.6; H, 2.4; N, 8.3; S, 12.6; K, 15.7% $C_{12}H_9N_3S_2O_8K_2.2H_2O$ requires: C, 28.8; H, 2.6; N, 8.4; S, 12.8; K, 15.6%.

The product can be shown by thin-layer chromatography and by diazo coupling reactions to be different in structure to the known 2-nitro-4'-aminodiphenylamine-3',-disulphonic acid which is prepared by the condensation of 3-nitro-4-chlorobenzenesulphonic acid with 2,5-diaminobenzenesulphonic acid.

EXAMPLE 2

70 Parts of 2-nitro-4'-acetylaminodiphenylamine-4-sulphonic acid are added slowly to 730 parts of 100% sulphuric acid keeping the reaction temperature below 10° C. by external cooling. 378 Parts of 20% oleum are added dropwise to the mixture which is then stirred at 20°–25° C. for 2 hours. The mixture is poured onto 5000 parts of ice, with stirring and the resulting mixture is heated to 75° C. and stirred at this temperature for 2 hours. The solution is then cooled to 20°–25° C. and barium carbonate is added until the mixture is neutral to Congo Red indicator paper. The precipitate of barium sulphate is removed by screening and sodium carbonate is then added to the filtrates until the mixture is faintly alkaline to Brilliant Yellow indicator paper. The suspension is then screened and the filtrates are evaporated to dryness. The residue is suspended in 3000 parts of methanol and screened from inorganic salts. The filtrates are then evaporated to dryness to give 92 parts of 2-nitro-4'-aminodiphenylamine-2',4-disulphonic acid identical in all respects with the product prepared as described in Example 1.

EXAMPLE 3

15 Parts of 4'-amino-2-nitrodiphenylamine-4-sulphonic acid are dissolved in 180 parts of 20% oleum at 0°–5° C. The mixture is stirred at 0°–5° C. for 2 hours when sulphonation is complete as judged by T.L.C. The product is isolated as described in Example 2 to give 4'-amino-2-nitrodiphenylamine-2',4-disulphonic acid identical in all respects to that obtained by the process of Example 2.

EXAMPLE 4

15 Parts of 4'-amino-2-nitrodiphenylamine-4-sulphonic acid in 170 parts of 95% sulphuric acid are heated at 80° C. for 2 hours. The product is isolated as described in Example 2 to give 4'-amino-2-nitrodiphenylamine-2',4-disulphonic acid acid identical to that obtained by the process of Example 2.

I claim

1. 2-Nitro-4'-aminodiphenylamine-2',4-disulphonic acid.

2. A method for the preparation of the compound claimed in claim 1 which comprises reacting 2-nitro-4'-aminodiphenylamine-4-sulphonic acid or 2-nitro-4'-acetylaminodiphenylamine-4-sulphonic acid with sulphuric acid having a strength of at least 95% or oleum of up to 20% strength at a temperature in the range of $-10°$ to 80° C.

3. A method as claimed in claim 2 which uses sulphuric acid of 100% strength or oleum of up to 10% strength at a temperature in the range of 0° to 25° C.

* * * * *